United States Patent [19]
Lands et al.

[11] Patent Number: 5,738,648
[45] Date of Patent: Apr. 14, 1998

[54] METHOD AND APPARATUS FOR A VALVE AND IRRIGATOR

[75] Inventors: Michael J. Lands, Louisville; James J. Podracky, Denver; Thomas P. Ryan, Fort Collins; Dale F. Schmaltz, Boulder, all of Colo.

[73] Assignee: Valleylab Inc, Boulder, Colo.

[21] Appl. No.: 590,233

[22] Filed: Jan. 23, 1996

[51] Int. Cl.⁶ .................................................. A61M 1/00
[52] U.S. Cl. ........................... 604/35; 604/902; 604/118
[58] Field of Search ................................ 604/30, 35, 118, 604/119, 902

[56] References Cited

U.S. PATENT DOCUMENTS

| | | | |
|---|---|---|---|
| 1,889,425 | 11/1932 | Sorensen | 604/119 X |
| 3,828,780 | 8/1974 | Morrison, Jr. | |
| 4,278,083 | 7/1981 | Young et al. | |
| 4,287,889 | 9/1981 | Stupar | 604/119 |
| 4,337,770 | 7/1982 | Young et al. | |
| 4,356,823 | 11/1982 | Jackson | 604/35 X |
| 4,387,879 | 6/1983 | Tauschinski | |
| 4,534,542 | 8/1985 | Russo | 604/902 X |
| 4,686,981 | 8/1987 | Forintos | |
| 4,692,140 | 9/1987 | Olson | 604/119 X |
| 4,842,591 | 6/1989 | Luther | |
| 4,874,377 | 10/1989 | Newgard et al. | |
| 5,098,395 | 3/1992 | Fields | |
| 5,255,676 | 10/1993 | Russo | 604/119 X |
| 5,447,494 | 9/1995 | Dorsey, III | 604/118 X |

*Primary Examiner*—Sam Rimell
*Assistant Examiner*—Luke J. Yeh
*Attorney, Agent, or Firm*—Peter C. Richardson; Lawrence C. Akers; Aaron Passman

[57] ABSTRACT

A valve and irrigator used with a suction tube has an elongate funnel with an axis through an enlarged entrance and an opposed extended exit duct of a flexible elastomer. A flow passage through the elongate funnel connects the entrance to the exit permitting fluid communication. A web across and near the enlarged entrance sealingly separates that from the exit. The web and the elongate funnel are made of silicone elastomer and are adhesively adhered to together. A portal in the web passes therethrough along the axis and is circular in shape to surround in fluid tight engagement the suction tube. A lid, proximally of the web on the enlarged entrance, has an inlet for irrigation and a pass through for the tube; the lid closes the enlarged entrance forming a chamber between the web and the lid. A slit within the web, near the portal and spaced from the axis is in the form of a closed mouth composed of a pair of sealing lips. Normally the pair of lips are together but are able to separate and define a passageway for fluid flow through the web. A peripheral bump is radially disposed relative to the slit and is located on the entrance in position to align flexure force therethrough and toward the axis. A method of using the valve and irrigator with the suction tube has steps including locating an elongate funnel along the axis with the entrance thereon. Positioning the exit on the elongate funnel opposite the entrance and along the axis is a step. Merging the exit with the entrance is step. A step is permitting fluid communication through the flow passage between the entrance and exit. Sealingly separating the entrance and exit with the web is a step. The step of passing the portal through the web along the axis so it surrounds tube therethrough. A method for making the valve and irrigator has steps of locating the web near the entrance, passing through the web the portal and slit.

15 Claims, 3 Drawing Sheets

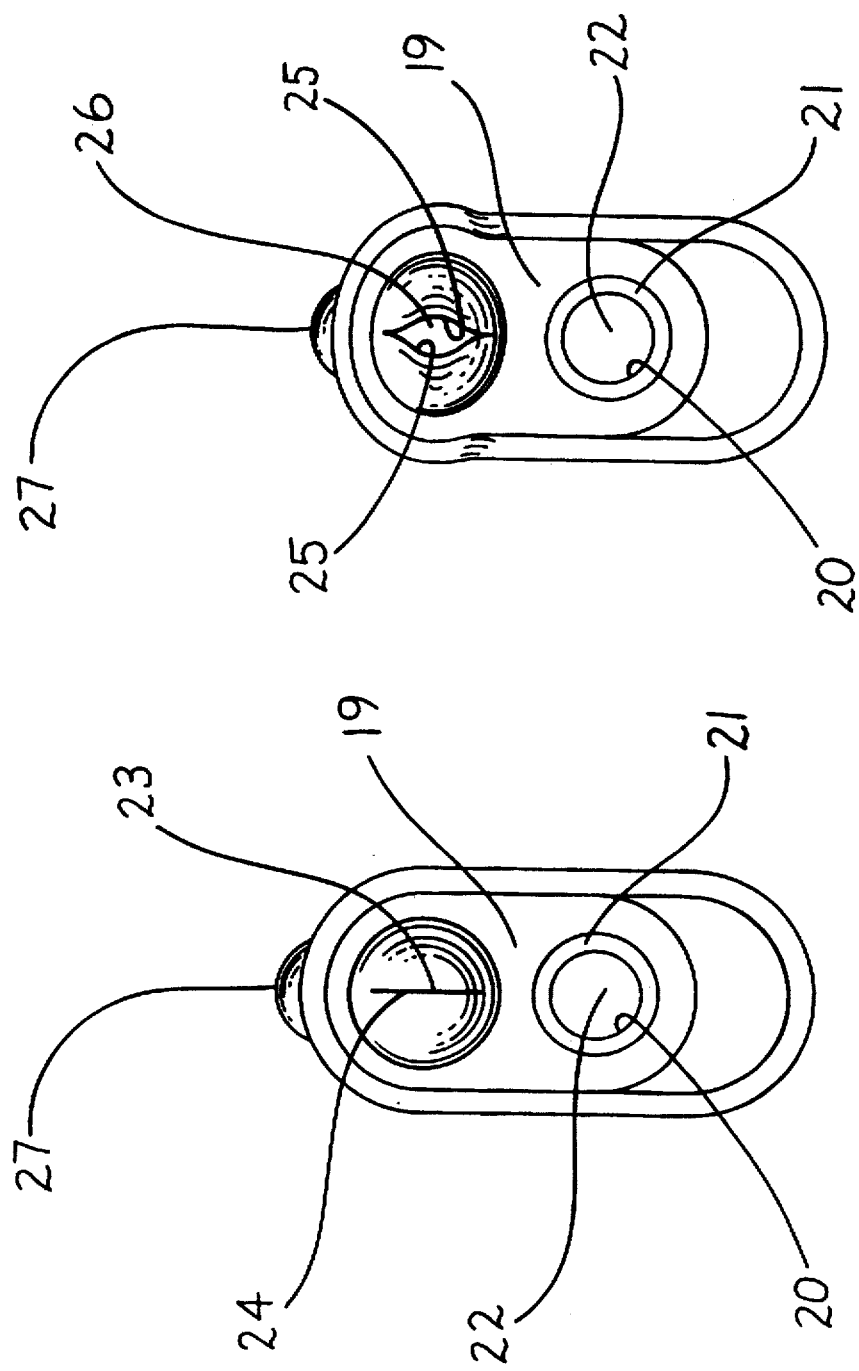

METHOD AND APPARATUS FOR A VALVE AND IRRIGATOR

FIELD OF THE INVENTION

This relates to a valve and irrigator for use with a suction tube. More particularly, the suction tube fits coaxially through the irrigator with the valve adjacent thereto for controlling irrigant flow.

BACKGROUND OF THE DISCLOSURE

In neurosurgery, the surgeon controls the flow of irrigant to the surgical site to flush away blood, debris and other bodily fluids for clear observation of the specific area of interest. Much as a dentist does the irrigation is sprayed with one instrument and the suction or drainage is another. Unlike the dentist, the neurosurgeon can not merely hook the suction over a lip and leave it there to remove that which puddles in a low spot. Consequently, a two handed approach is common. Specifically one hand controls the irrigation direction and the other the suction. The Frazier suction tube is commercially available and is preferred; it is made of metal and has a finger plate for a control orifice. Thus the elongate tube connects to a suction source proximally and has a distal end with a blunt collar to protect tissue near the operative site. A passage extends between the ends and through the Suction tube interrupted by the orifice through the finger plate. The surgeon can thus cover the finger plate orifice and have full suction at the distal end or let the suction open to bleed it off. A similar device in U.S. Pat. No. 3,828,780 wherein a vacuum finger port is shown. U.S. Pat. No. 4,686,981, has a large hole and a small hole in the finger plate to adjust the bleed off level.

U.S. Pat. No. 4,387,879 has a connector with a flow passage blocked by an elastomeric disc having a central slit positioned to permit the unobstructed cannula or catheter movement therethrough. U.S. Pat. No. 4,842,591 has a fitting closed internally by deformable septum with a slit. The normally closed slit can be opened by a moveable plug captured within the fitting and the plug poised proximally to the septum in position for pressing against it to open the slit.

U.S. Pat. No. 4,874,377 has a cannula assembly with an occluding means therein to permit insertion in an over the needle procedure. Thereafter, flow through the occluding means occurs when an infusion and/or monitoring tube connects proximally and deforms the occluding means. U.S. Pat. No. 5,098,395 has a two part medical connector, one having a septum and the other a needle. The septum defines a flashback chamber to determine a successful stick by means of a notch in the needle disposed in the flashback chamber.

U.S. Pat. Nos. 4,278,083 and 4,337,770 have a flow regulator with a coaxial plug including a restriction passage therethrough and a flexible conduit sealed thereabout. The flexible conduit seal breaks when squeezed thereby bypassing the restriction passage. Flow passes through the restriction until the flexible conduit is squeezed thereafter unrestricted flow occurs.

Not one of the prior valve arrangements has been combined with or adapted to be used with a suction tube for facilitating a one handed technique for irrigation and suction. None of the mentioned patents suggest a valve and irrigator for suction and irrigation when used with a Suction tube. The method of making the combination of a Suction tube with an irrigator coaxially thereabout and the method of using the combination are unknown in the prior patents.

SUMMARY OF THE INVENTION

A valve and irrigator for use in combination with a suction tube may have an elongate funnel. The elongate funnel has an axis through an enlarged entrance and an extended exit duct opposite the enlarged entrance and along the axis. The extended exit duct most preferably merges with the enlarged entrance. In the preferred embodiment the exit duct is made of a flexible elastomer so the suction tube therethrough when bent will flex the exit duct to angle thereof that is off axis therealong. A flow passage through the elongate funnel may connect the enlarged entrance to the extended exit duct for permitting fluid communication therethrough. A conical cavity is preferred between the enlarged entrance and the merger with the extended exit duct. A web might be across the cavity near the enlarged entrance for preferably sealingly separating the enlarged entrance from the extended exit duct. In the preferred embodiment the web is substantially normal to the axis.

The web and the elongate funnel may be made of silicone elastomer and are molded together. The web is preferably bonded within the cavity near the enlarged entrance. A portal in the web most preferably passes therethrough along the axis. The portal can be circular in shape and could surround in fluid tight engagement the suction tube placed therethrough. The portal in the preferred embodiment includes a cuff having an opening to receive the suction tube. A slit within the web, near the portal and spaced from the axis, may be in the form of a closed mouth composed of a pair of sealing lips. Normally the pair of lips are together but are able to separate and define a passageway for fluid flow through the web.

A peripheral bump in the preferred embodiment may be radially disposed relative to the slit. The peripheral bump is preferably located on the enlarged entrance in position to align flexure force therethrough and toward the axis. The force distorts the pair of lips into a pursed shape and therefore open configuration from their normally closed position. The orientation of the portal and the peripheral bump are preferably substantially diametrical with respect to one another and the axis. Proximally of the web is a lid over the enlarged entrance. The lid has an inlet for the irrigation from an infusion bag and a pass through for the suction tube. The lid closes the enlarged entrance forming a chamber between the web and the lid. The chamber acts as a reservoir for the irrigation before it passes through the open slit passageway. Thus, force on the peripheral bump releases back pressure due to the head caused by the bag connected through inlet to the chamber.

A method of using the valve and irrigator with the suction tube has steps preferably including locating the elongate funnel along the axis with the enlarged entrance on the elongate funnel. Positioning an extended exit duct on the elongate funnel opposite the enlarged entrance and along the axis may be a step in the preferred method. Merging the extended exit duct with the enlarged entrance could be another method step. A step in the method may include permitting fluid communication through the flow passage of the elongate funnel between the enlarged entrance and the extended exit duct. Sealingly separating the cavity between the enlarged entrance and the merger with the extended exit duct with the web across the enlarged entrance is a step in the method of preference. The preferred method may have the step of passing the portal through the web along the axis so the portal may surround in fluid tight engagement the suction tube placed therethrough. Spacing the slit within the web, near the portal but from the axis with the slit in the form of a closed mouth composed of a pair of sealing lips normally together but able to separate to define the passageway for fluid flow through the web might occur with a method step. The method of using might preferably include the step of passing the suction tube through portal then bending it to flex the exit duct to angle therewith off axis therealong.

The method may preferably include the step of disposing radially on the enlarged entrance a peripheral bump. The bump is in position to align flexure force therethrough and toward the axis to distort the pair of lips into a pursed and therefore open configuration from their normally closed position.

A method for making a valve and irrigator in the elongate funnel with the enlarged entrance and the extended exit duct opposite and merging with the enlarged entrance in a flow passage connects the enlarged entrance to the extended exit duct for permits fluid communication therethrough and along an axis for use in combination with a suction tube. The method comprising the preferred steps adhering the web near the enlarged entrance for sealingly separating the enlarged entrance from the extended exit duct. Passing through the web the portal located along the axis and positioning a slit within the web, near the portal and spaced from the axis are preferred steps of the method. The slit may act as a closed mouth composed of a pair of sealing lips normally together but able to separate and define a passageway for fluid flow through the web. The method may have the step of making wherein the enlarged entrance, the web and the exit duct are fashioned preferably of a flexible elastomer by molding.

BRIEF DESCRIPTION OF THE DRAWINGS

FIG. 3 are two views of the valve and irrigator of FIG. 1 as would be seen along cut lines 3—3 in FIG. 1; the two views illustrate the slit valve closed and open.

DETAILED DESCRIPTION OF THE INVENTION

Figure 1:
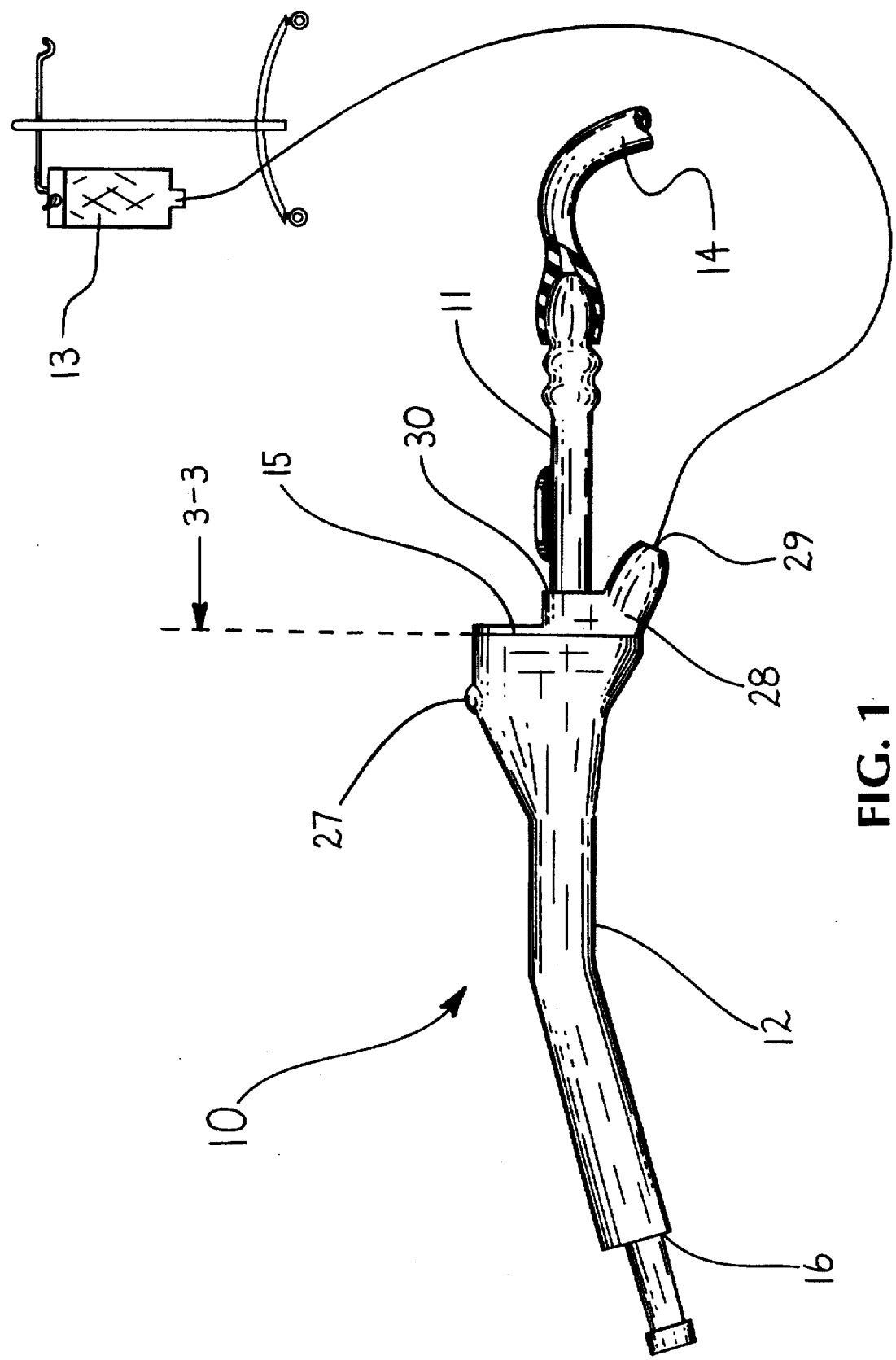
FIG. 1 is a perspective view of a valve and irrigator illustrated as connected to a suction hose and a supply bag for irrigant.
Figure 2:
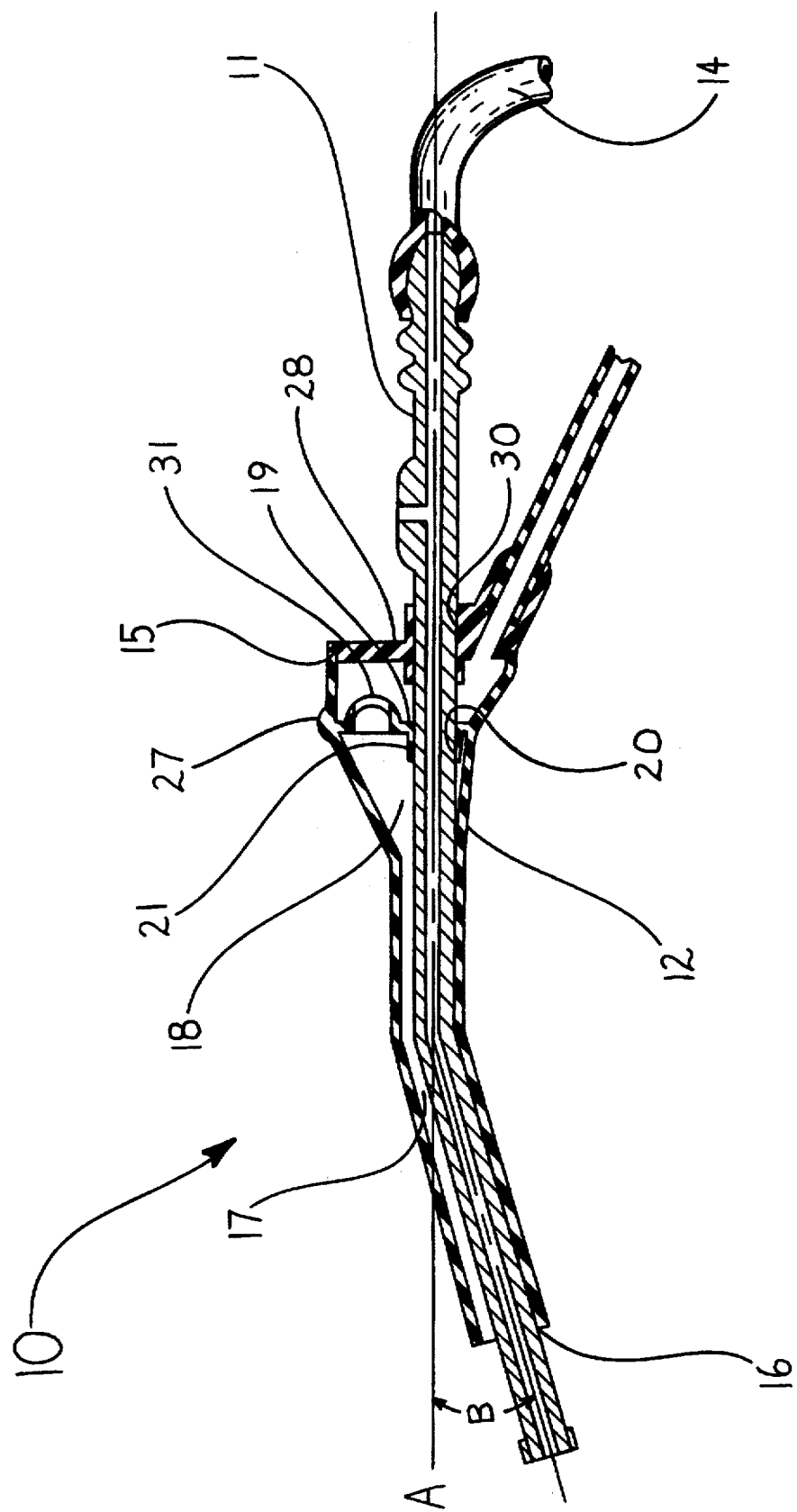
FIG. 2 is a side view in the cross section of the valve and irrigator shown in FIG. 1 as would appear if cut in half along line 2—2 shown in FIG. 1.

A valve and irrigator 10 for use in combination with a suction tube 11 has an elongate funnel 12. In FIG. 1 a perspective view of the set up for the valve and irrigator 10 showing it connected to an irrigation bag 13 and a piece of suction hose 14. The elongate funnel 12 has an axis "A" through an enlarged entrance 15 and an extended exit duct 16 opposite the enlarged entrance 15 and along the axis "A" as shown in FIGS. 1 and 2. The extended exit duct 16 merges with the enlarged entrance 15. In the preferred embodiment the extended exit duct 16 is made of a flexible Dow Corning silicone elastomer Q7-4850 so the metal suction tube 11 therethrough when bent will flex the extended exit duct 16 to angle "B" thereof that is off axis "A."

A flow passage 17 in the side cross sectional view of FIG. 2 through the elongate funnel 12 connects the enlarged entrance 15 to the extended exit duct 16 for permitting fluid communication therethrough. A conical cavity 18 is shown in FIG. 2 and preferred but any shape of the cavity 18 between the enlarged entrance 15 and the merger with the extended exit duct 16 will suffice. A web 19 across the cavity 18 near the enlarged entrance 15 sealingly separates the enlarged entrance 15 from the extended exit duct 16. As will be explained herein the sealingly separating is subject to permitted movement of irrigant and suction in a controlled and desirable fashion. In the preferred embodiment the web 19 is substantially normal to the axis "A" as seen in FIG. 2.

The web 19 and the elongate funnel 12 are made of the same type of silicone elastomer previously identified and are molded together as one piece. The web 19 fits within the cavity 18 near the enlarged entrance 15 as opposed to across whereat there is the merger with the extended exit duct 16.

A portal 20 in the web passes therethrough along the axis "A." The portal 20 is circular in shape for surrounding in fluid tight engagement the suction tube 11 placed therethrough. The portal 20 in the preferred embodiment includes a cuff 21 having an opening 22 to receive the suction tube 11. A slit 23 within the web 19, near the portal 20 and spaced from the axis "A," forms a closed mouth 24 composed of a pair of sealing lips 25. Normally the pair of lips 25 are together but are able to separate and define a passageway 26 for fluid flow through the web 19. The open and separated lips 25 are shown in FIG. 3 a view of the web 19 as seen along the line 3—3 of FIG. 1. Irrigation from the bag 13 shown in FIG. 1 is controlled by the valve action of the slit 23 in FIG. 3.

A peripheral bump 27 in the preferred embodiment is radially disposed relative to the slit 23. The peripheral bump 27 is located on the enlarged entrance 15 in position to align flexure force applied by the neurosurgeon therethrough and toward the axis "A." The force distorts the pair of lips 25 into a pursed shape, as in FIG. 3, and therefore open configuration from their normally closed position. The orientation of the portal 20 and the peripheral bump 27 are diametrical with respect to one another and the axis "A."

Proximally of the web 19 is a lid 28 in FIGS. 1 and 2 over or across the enlarged entrance 15. The lid 28 has an inlet for the irrigation from bag 13 and a pass through 30 for the suction tube 11. As best understood from FIG. 2, the lid 28 closes the enlarged entrance 15 forming a chamber 31 between the web 19 and the lid 28. The chamber 31 acts as a reservoir for the irrigation before it passes through the open slit 23 passageway 26 (in FIG. 3). Thus, force on the peripheral bump 27 releases back pressure due to the head caused by the bag 13 connected through inlet 29 to the chamber 31.

A method of using the valve and irrigator 10 with the suction tube 11 has steps preferably including locating the elongate funnel 12 along the axis "A" with the enlarged entrance 15 on the elongate funnel 12. Positioning the extended exit duct 16 on the elongate funnel 12 opposite the enlarged entrance 15 and along the axis "A" is a method step. Merging the extended exit duct 16 with the enlarged entrance 15 is another method step. A step in the method includes permitting fluid communication through the flow passage 17 of the elongate funnel 12 between the enlarged entrance 15 and the extended exit duct 16.

Sealingly separating the cavity 18 between the enlarged entrance 15 and the merger with the extended exit duct 16 with the web 19 across the enlarged entrance 15 is a step in the method. The method has the step of passing the portal 20 through the web 19 along the axis "A" so the portal 20 surrounds in fluid tight engagement the suction tube 11 placed therethrough. Spacing the slit 23 within the web 19, near the portal 20 but from the axis "A" with the slit 23 in the form of a closed mouth composed of the pair of sealing lips 25 normally together but able to separate to define the passageway 26 for fluid flow through the web 19 occurs with a method step. The method of using includes the step of passing the suction tube 11 through portal 20 then bending it to flex the extended exit duct 16 to angle "B" therewith off axis "A" therealong.

The method includes the step of disposing radially on the enlarged entrance 15 the peripheral bump 27. The peripheral bump 27 aligns flexure force therethrough and toward the axis "A" to distort the pair of lips 25 into a pursed shape and therefore open configuration from their normally closed position as shown in FIG. 3.

A method for making the valve and irrigator 10 in the elongate funnel 12 with the enlarged entrance 15 and the extended exit duct 16 opposite and merging with the enlarged entrance 15 in the flow passage 17 connects the enlarged entrance 15 to the extended exit duct 16 for permitting fluid communication therethrough and along the axis "A" for use in combination with the suction tube 11. The method comprises the step of adhering the web 19 near the enlarged entrance 15 for sealingly separating the enlarged entrance 15 from the extended exit duct 16. Passing through the web 19 the portal 20 located along the axis "A" and positioning the slit 23 within the web 19, near the portal 20 and spaced from the axis "A" are steps of the method. The slit 23 acts as a closed mouth composed of the pair of sealing lips 25 normally together but able to separate and define the passageway 26 for fluid flow through the web 19. The method has the step of making wherein the enlarged entrance 15, the web 19 and exit duct 16 are fashioned of a flexible elastomer by molding.

While a particular preferred embodiment has been illustrated and described the scope of protection sought is in the claims that follow.

What is claimed is:

1. A valve and irrigator for use in combination with a suction tube and an infusion bag with irrigant, the valve and irrigator comprising:

an elongate funnel having an axis;

an enlarged entrance on the elongate funnel;

an extended exit duct on the elongate funnel opposite the enlarged entrance and along the axis, the extended exit duct merging with the enlarged entrance;

a flow passage through the elongate funnel, the flow passage connecting the enlarged entrance to the extended exit duct for permitting fluid communication therethrough;

a merger between the enlarged entrance and the extended exit duct;

a cavity between the enlarged entrance and the merger with the extended exit duct;

a web across the cavity near the enlarged entrance for sealingly separating the enlarged entrance from the extended exit duct;

a portal in the web and passing therethrough, the portal located along the axis;

a lid disposed proximally of the web and across the enlarged entrance, the lid having an inlet for irrigation from an infusion bag and a pass through for a suction tube, the lid closing the enlarged entrance and forming a chamber between the web and the lid, and a slit within the web, near the portal and spaced from the axis, the slit as a closed mouth composed of a pair of sealing lips normally together but able to separate and define a passageway for fluid flow through the web.

2. The valve and irrigator of claim 1 wherein the elongate funnel, the lid and the web are made of an elastomer.

3. The valve and irrigator of claim 1 wherein the portal is circular in shape and surrounds in fluid tight engagement the suction tube.

4. The valve and irrigator of claim 1 wherein the enlarged entrance includes a peripheral bump radially disposed relative to the slit in position to align flexure force therethrough and toward the axis to distort the pair of lips into a pursed shape and therefore open configuration from their normally closed position.

5. The valve and irrigator of claim 1 wherein the web is molded within the cavity near the enlarged entrance.

6. The valve and irrigator of claim 1 wherein the exit duct is made of a flexible elastomer so the suction tube if bent will flex the exit duct to angle therewith off axis therealong.

7. The valve and irrigator of claim 1 wherein the elongate funnel and the web are made of silicone elastomer and are molded together.

8. The valve and irrigator of claim 7 wherein the web is substantially normal to the axis.

9. The valve and irrigator of claim 8 wherein the portal includes a cuff having an opening to receive the suction tube.

10. The valve and irrigator of claim 1 wherein the orientation of the portal and the peripheral bump are substantially diametrical with respect to one another and the axis.

11. A valve and irrigator for use in combination with a suction tube and irrigation, the valve and irrigator comprising:

an elongate funnel having an axis;

an enlarged entrance on the elongate funnel;

an extended exit duct on the elongate funnel opposite the enlarged entrance and along the axis, the extended exit duct merging with the enlarged entrance, the exit duct is made of a flexible elastomer so the suction tube therethrough when bent will flex the exit duct to angle therewith off axis therealong;

a flow passage through the elongate funnel, the flow passage connecting the enlarged entrance to the extended exit duct for permitting fluid communication therethrough;

a merger between the enlarged entrance and the extended exit duct;

a cavity between the enlarged entrance and the merger with the extended exit duct;

a web across the cavity near the enlarged entrance for sealingly separating the enlarged entrance from the extended exit duct, the web is substantially normal to the axis, the web and the elongate funnel are made of silicone elastomer and are adhesively adhered to together, the web is bonded within the cavity near the enlarged entrance;

a portal in the web, the portal passing therethrough along the axis, the portal is circular in shape and surrounds in fluid tight engagement the suction tube placed therethrough, the portal includes a cuff having an opening to receive the suction tube;

a lid disposed proximally of the web and across the enlarged entrance, the lid having an inlet for receiving irrigation and a pass through for the suction tube, the lid closing the enlarged entrance forming a chamber between the web and the lid, and a slit within the web, near the portal and spaced from the axis, the slit in the form of a closed mouth composed of a pair of sealing lips normally together but able to separate and define a passageway for fluid flow through the web, and a peripheral bump radially disposed relative to the slit and on the enlarged entrance in position to align flexure force therethrough and toward the axis to distort the pair of lips into a pursed and therefore open configuration from their normally closed position, the orientation of the portal and the peripheral bump are substantially diametrical with respect to one another and the axis.

12. A method of using a valve and irrigator with a suction tube, the method comprising the following steps:

locating an elongate funnel along an axis with an enlarged entrance on the elongate funnel;

positioning an extended exit duct on the elongate funnel opposite the enlarged entrance and along the axis;

merging the extended exit duct with the enlarged entrance;

permitting fluid communication through a flow passage of the elongate funnel between the enlarged entrance and the extended exit duct;

sealingly separating a cavity between the enlarged entrance and a merger with the extended exit duct with a web across the enlarged entrance;

passing a portal through the web along the axis so the portal surrounds in fluid tight engagement the suction tube placed therethrough;

spacing a slit within the web, near the portal so the slit is spaced from the axis with the slit in the form of a closed mouth composed of a pair of sealing lips normally together but able to separate and define a passageway for fluid flow through the web, and disposing radially on the enlarged entrance a peripheral bump in position to align flexure force therethrough and toward the axis to distort the pair of lips into a pursed shape and therefore open configuration from their normally closed position.

13. The method of using of claim 12 wherein therein is the step of bending the exit duct to angle off axis.

14. A method for making a valve and irrigator in an elongate funnel with an enlarged entrance and an extended exit duct opposite and merging with the enlarged entrance in a flow passage connecting the enlarged entrance to the extended exit duct for permitting fluid communication therethrough and along an axis for use in combination with a suction tube, the method comprising the steps of:

sealingly separating an enlarged entrance from an extended exit duct with a web near the enlarged entrance;

passing through the web a portal located along an axis, and positioning a slit within the web, near the portal and spaced from the axis, the slit as a closed mouth composed of a pair of sealing lips normally together but able to separate and define a passageway for fluid flow through the web.

15. The method of claim 14 with the step of making the elongate funnel and web of a flexible elastomer by molding.

* * * * *